United States Patent [19]
Lieberman et al.

[11] Patent Number: 5,006,329
[45] Date of Patent: Apr. 9, 1991

[54] RADIOACTIVE TAGGED COMPOUNDS AND METHOD FOR THE TREATMENT OF METASTATIC BONE CANCER

[75] Inventors: Ephraim Lieberman, Suffern; Maurice Bordoni, Westtown; Alfred Thornton, New Hampton, all of N.Y.

[73] Assignee: Cadema Medical Products, Inc., Middleton, N.Y.

[21] Appl. No.: 301,546

[22] Filed: Jan. 26, 1989

Related U.S. Application Data

[63] Continuation-in-part of Ser. No. 147,608, Jan. 22, 1988, abandoned.

[51] Int. Cl.$^5$ .......................... A61K 43/00; C07F 9/00
[52] U.S. Cl. ......................................... 424/1.1; 534/10
[58] Field of Search ........................... 424/1.1; 534/10

[56] References Cited

U.S. PATENT DOCUMENTS 4,452,774  6/1984  Jones et al. .................... 424/1.1
4,533,541  8/1985  Srivastava et al. ............. 424/1.1

*Primary Examiner*—Robert L. Stoll
*Assistant Examiner*—Cynthia Harris
*Attorney, Agent, or Firm*—Leonard Bloom

[57] ABSTRACT

Organophosphonates such as methylene diphosphonates and analogs thereof are tagged with chromium-51 for the treatment of bone cancer without causing damage to bone marrow. The chromium-51 organophosphonates seek out, attach to, and treat bone tumors with high specificity.

30 Claims, No Drawings

RADIOACTIVE TAGGED COMPOUNDS AND METHOD FOR THE TREATMENT OF METASTATIC BONE CANCER

CROSS REFERENCE TO RELATED APPLICATION

The present application is a continuation-in-part application of copending application Ser. No. 147,608, filed Jan. 22, 1988, abandoned.

FIELD OF THE INVENTION

The present invention relates to a compound and a method for the treatment of bone cancer, and more particularly, to a compound and method for the treatment of metastatic bone lesions.

BACKGROUND OF THE INVENTION

At the present time, the treatment of metastatic bone cancer (malignant tumors or lesions) is usually ineffective. Direct radiation therapy is usually ineffective. The patient undergoing radiation therapy suffers excruciating pain and eventually dies. During the disease, morphine injections are continually administered in an attempt to alleviate the pain and suffering. If the treatment involves chemotherapy, there are side effects which are very undesirable. Furthermore, chemotherapy is not often effective.

The effects of metastatic bone cancer are particularly devastating when the bone cancer appears after an ostensibly successful treatment of another form of cancer, such as breast cancer or prostate cancer. For as yet unknown reasons, hormonal cancers such as breast and prostate cancer have a tendency to metastasize to bring about bone tumors. It would certainly be desirable to increase the cure rate of breast and prostate cancers by successfully treating metastatic bone cancer.

In the diagnosis and treatment of certain cancers, radioactive tagged particles have been resorted to in the prior art. For the most part, however, this method has been limited to the treatment of cancers of the cervix or ovaries. The use of these existing radioactive tagged particles are wholly unsatisfactory for the treatment of bone cancer.

Radioactive tagged compounds, when administered to a patient, may not have a high degree of specificity for the malignant lesion. As a result, unwanted radiation is delivered to other parts of the body, thereby destroying healthy tissue. Even if the tagged compound is organ specific, it often does not have a high affinity for the lesion itself, thereby destroying healthy tissue in the organ.

Agents have been tried in the past that employ radioactive labelled agents that seek out cancerous bone tissue when administered systemically. For example, Dr. Ralph Robinson, University of Kansas Medical Center, Kansas City, Mo., has treated over 100 patients with Strontium-89 for treatment of metastatic bone cancer. His results are acceptable from the standpoint of effectiveness in treating the cancer; however, the results are not acceptable from the standpoint of safety. More specifically, the degree of malignancy is reduced and the pain is reduced; however, the dose of radioactivity to bone marrow is unacceptably high. The radioactive emissions from Strontium-89 include high energy beta emissions (e.g. 800KeV) that are sufficiently energetic to penetrate through bone to bone marrow. The high levels of beta emissions account for Strontium-89 as being unacceptable from the standpoint of safety to healthy bone marrow tissues. Furthermore, Strontium-89 has a 54-day half-life which is undesirably long.

In another use of radioactive labelled agents for treating bone cancer by systemic administration, Dow Chemical Company and researchers at the University of Missouri reactor are using a bone treating agent (hydroxymethyldisphonate, HMDP) to which they attach a Samarium-153 label. Preliminary results appear promising from the standpoint of effectiveness in treating the malignancy; however, the results are indeterminate from the standpoint of safety with respect to healthy bone marrow tissue. The radioactive emissions from Samarium-153 include a large portion of high energy beta emissions (e.g. 600–700 KeV) that are sufficiently energetic to penetrate through the bone and enter the highly sensitive bone marrow where they can do considerable damage such as bringing about aplastic anemia or leukemia. The high levels of beta emissions account for Samarium-153 as being unacceptable from the standpoint of safety to healthy bone marrow tissues even though the half-life of Samarium-153 is approximately only two days.

In the case of bone cancer, we have noted that even if the radioactive tagged compound does have a high affinity for the malignant tissue, it is imperative that the radioactive tagged compound does not emit high energy particles such as high energy beta particles. These high energy particles will penetrate to the bone marrow, thereby causing radiation damage which is undesirable. Bone marrow is highly susceptible to being damaged by radiation, and it is imperative that radiation treatment of malignant bone tissue does not damage the bone marrow.

SUMMARY OF THE INVENTION

We have discovered that organophosphonates, such as methylene diphosphonates and analogs thereof, when labelled or tagged with chromium-51, have particular utility in the detection, localization and treatment of bone cancer. These Cr-51 tagged organophosphonate compounds are highly specific for malignant bone tissue and, in effect, are excellent carriers for the chromium-51. Moreover, because chromium-51 does not emit high energy beta particles but lower energy Auger electrons (e.g. 4 KeV), there is minimal energy that can penetrate through hard bone tissue and do damage to the bone marrow and surrounding tissue. Furthermore, the half-life of chromium-51 is 27 days.

In addition, since chromium-51 is also a gamma emitter, it can be determined whether the tagged compounds are at the proper site in the patient's body. This is a supplementary advantage of the present invention.

Accordingly, it is the primary object of this invention to provide radioactive compounds useful in the treatment of metastatic bone cancer.

It is another object of this invention to provide radioactive labelled compounds having a high affinity for malignant bone tissue thereby preferentially attaching to malignant bone tissue and not attaching to healthy tissues.

Another object of the invention is to provide radioactive compounds which remain localized at the site of a malignant bone lesion for a sufficient length of time to bring about effective treatment and do not injure bone marrow.

Still another object of the invention is to provide radioactive compounds which effectively shrink malignant bone tumors.

In accordance with the broad teachings of the present invention, a radioactive compound is provided, comprising a bone-seeking moiety and a chromium-51 moiety. Preferably, the bone-seeking moiety is an organophosphonate precursor of the formula

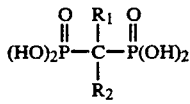 (Formula A)

wherein $R_1$ and $R_2$ may be hydrogen, an aliphatic hydrocarbon, an aromatic hydrocarbon or an alicyclic hydrocarbon; and wherein the methylene diphosphonate precursor is tagged with chromium-51. One of the R groups can also be an hydroxyl group.

More specifically, the compounds as represented by the following formulas may be employed consonant with the teachings of the present invention:

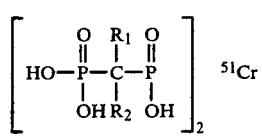 (Formula B)

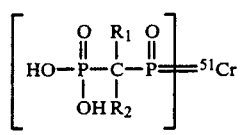 (Formula C)

The foregoing classes of radioactive compounds are particularly useful as therapeutic agents in the treatment of various types of cancer, and specifically, metastatic bone cancer.

For purposes of the present invention compounds, which may be represented by Formulas B and C or mixtures thereof above, are effective bone cancer treating radioactive compounds of the invention. The exact stoichiometry of the compounds need not be established to effect suitable administration of the compounds of the invention.

The present invention also provides an improved method of treating bone cancer. The method includes the steps of selecting a compound having an affinity for bone, and labelling or tagging the compound with a radioisotope which emits low energy Auger electrons and does not emit high energy beta particles which would be potentially harmful to surrounding healthy tissue especially bone marrow. The radioisotope has a half-life which facilitates preparation of the tagged compound at a central location and delivery of the same through available transportation channels. Thereafter, the tagged compound is administered conveniently to a patient in need thereof.

Preferably, in the improved method of the present invention, the precursor compound is a methylene diphosphonate, and the radioisotope is chromium-51.

Specifically preferred organophosphonate precursors are as follows:

(a) where $R_1$ is a hydroxyl group, and $R_2$ is a methygroup (EHDP);

(b) where $R_1$ and $R_2$ are the same group;

(c) where $R_1$ and $R_2$ are both hydrogen (MDP);

(d) where $R_1$ and $R_2$ are different; and (e) where $R_1$ is hydrogen, and $R_2$ is a methyl group.

Other bone-seeking moieties that can be used along with a Chromium-51 moiety may be inorganic or organic and include: hydroxy methyl diphosphonate (HMDP); polyphosphates; and organic diphosphonates generally.

The nature and substance of the present invention as well as its objects and advantages will be more clearly perceived and fully understood by referring to the following description and claims.

GENERAL DESCRIPTION OF THE PREFERRED EMBODIMENTS

The radioactive (or tagged) compounds of this invention have a particular utility in the treatment of various types of cancer, and specifically, metastatic bone cancer. The compounds are prepared by tagging a methylene diphosphonate or analogous compounds with the isotope chromium-51. (27.8 day T½)

The preferred organophosphonates useful in the practice of this invention have the general formula

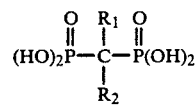 (Formula D)

wherein $R_1$ and $R_2$ may be hydrogen, an aliphatic hydrocarbon, an aromatic hydrocarbon or a napthenic hydrocarbon. $R_1$ and $R_2$ in any one compound may be the same or different. Examples of aliphatic hydrocarbon groups are methyl, ethyl, propyl, isopropyl, butyl, isobutyl and tertiary butyl groups. Examples of aromatic hydrocarbon groups are phenyl and tolyl groups. Examples of alicyclic groups are cyclopentyl and cyclohexyl groups. One of the R groups can also be an hydroxyl group.

The organophosphonates used in the practice of this invention are particularly well suited for the treatment as well as the detection and localization of malignant bone lesions. Not only do the organophosphonates have a high affinity for bone, but, more importantly, they have a particularly high affinity, by factors of 50 or more, for malignant bone tissue.

The following Example 1 represents the preferred method of preparing the organophosphonate-51Cr compounds of the invention:

EXAMPLE 1

Initially, the diphosphonate of the chemical structure:

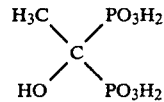 (Formula E)

is obtained. This methylene diphosphonate is generally referred to as disodium 1-hydroxyethane-1, 1-diphosphonate (EHDP). Its accepted Chemical Abstracts name is 1-hydroxyethlidene, bis [phosphonic acid].

10 milligrams of EHDP is then dissolved in 0.2 ml aqueous solution of 0.9% NaCl within a vial, preferably a serum finish type 1 glass vial. To this solution, a 0.01 ml solution of chromium-51 (200 Ci) as the chromous chloride (Cr$^{2+}$) is added. This solution is then mixed. To this mixture, a 0.8 ml solution of 0.9% NaCl is added. All of the aforementioned preparation steps occur at room temperature.

The vial is then stoppered and submerged in a hot water bath of approximately 96° C. for 35-40 minutes. The vial is then removed from the water bath and permitted to cool to room temperature. The product obtained is $^{51}$Cr tagged EHDP. The radioactive drug represented as either formula F or formula G below is then ready for use.

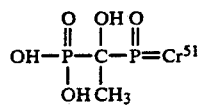
(Formula F)

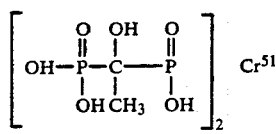
(Formula G)

EXAMPLE 2

Initially, the diphosphonate of the chemical structure:

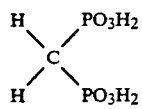
(Formula H)

is obtained. This methylene diphosphonate is generally referred to as disodium methylene-diphosphonate (MDP).

10 milligrams of MDP is then dissolved in 0.2 ml aqueous solution of 0.9% NaCl within a vial, preferably a serum finish type 1 glass vial. To this solution, a 0.01 ml solution of chromium-51 (200 Ci) as the chromous chloride (Cr$^{2+}$) is added. This solution is then mixed. To this mixture, a 0.8 ml solution of 0.9% NaCl is added. All of the aforementioned preparation steps occur at room temperature.

The vial is then stoppered and submerged in a hot water bath of approximately 96° C. for 35-40 minutes. The vial is then removed from the water bath and permitted to cool to room temperature. The product obtained is $^{51}$Cr tagged MDP. The radioactive drug represented as either formula I or formula J below is then ready for use.

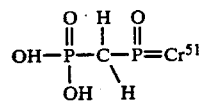
(Formula I)

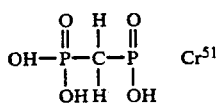
(Formula J)

The exact nature of the bond between Cr-51 and the organophosphonate moiety is not known for certain. The compounds of the invention may have been ionic and covalent character. A theoretical description of the bonds is not necessary for using the compounds of the invention in accordance with the specification herein. Other diphosphonates that may be employed in carrying out the invention include di-chloro methylene diphosphonate and 1-amino-ethane-1, 1-diphosphonate.

Inorganic polyphosphates, such as pyrophosphates (P$_2$O$_7$$^{-4}$), may also be employed as bone seeking moieties with the invention.

Suitable cations for forming the organic phosphonate and inorganic polyphosphate salts include sodium, potassium, magnesium, cesium, calcium, barium, and iron. It is to be understood, however, that any non-toxic salt forming cation may be used.

The following represents the preferred method of administering the organophosphonate-51Cr compounds of the invention in humans, to treat metastatic bone cancer:

Methods of Administration

First, imaging with technetium-99 (Tc-99m) of the subject is performed to show the presence of, and to outline the lesion, in a manner that is well known to those skilled in the art. It is contemplated that the dosage of Cr-51 diphosphonate to be administered for therapeutic purposes will result in a radiation amount of approximately 5,500-7,000 rads, although dosages are expected to vary greatly from patient to patient.

It is to be understood by those skilled in the art, that it is not contemplated herein that the entire dosage be delivered at one time, in one injection. Rather, it is contemplated that this dosage is to be administered over the entire course of treatment, and well known calculations of dosage can be employed.

The appropriate quantity of the compound (as determined by the aforesaid calculations) is then to be intravenously administered to the patient. While it is contemplated that this administration site is to be an arm vein, because the treatment is a systemic treatment, it is also contemplated that suitable veins in other parts of the body could alternatively be utilized.

It is contemplated that the administrations, as described above, are, preferably, to be performed once a day (5 days a week) for a period of approximately four to six weeks. Thus, if for example, the desired total dosage over the course of treatment is 500 millicuries, then one would inject approximately 25 millicuries of the compound per day for 20 days. During the course of treatment, the patient would be monitored for any adverse reactions that may result from the aforementioned treatment.

The radioactive compounds of this invention are prepared by tagging one of the above organophosphonate precursors with chromium-51. Chromium-51 is a unique radioisotope in that it emits no high energy beta particles, but it does have a high abundance of low energy Auger electrons in its decay scheme. This results in an energy emission of 93 millirads per disintegration. Thus, when chromium-51 is combined with a methylene diphosphonate of this invention, the resulting radioactive compound is capable of delivering a therapeutic dose of about 5,000-6,000 rads to a bone tumor or bone lesion. This level of radiation is highly useful in treating malignant conditions such as primary as well as metastatic bone lesions.

The production of chromium-51, involving the use of a nuclear reactor, is relatively simple and inexpensive. The chemistry of chromium-51 is well known, and the procedure for labelling or tagging organophosphonate compounds is generally well known to those skilled in the art and is described above in Example 1.

Chromium-51 has a half-life of 27.8 days. This allows the compounds to be tagged at a central facility and then shipped to hospitals, clinics or radiology centers using readily available transportation channels. As a result, the distribution and logistics problems are greatly simplified, as well as the ultimate disposal of the compounds, thereby facilitating the widespread commercialization of the invention.

Because chromium-51 emits low energy Auger electrons and no high energy beta particles, the radiation dose to bone marrow is significantly less than with other radioisotopes or other systems for radiation therapy. Since the bone marrow is very sensitive to radiation and is a very critical organ, it is important that radiation damage to bone marrow be kept to a minimum or, preferably, avoided entirely. Chromium-51 is therefore ideally suited to irradiate the tumor or lesion while sparing the bone marrow.

The desirable properties of chromium-51 are augmented by the properties of the methylene diphosphonates (and analogs thereof) which are not only highly specific to bone tissue but which have a very high affinity, by factors of 50 or more, for malignant bone tissue. Thus, not only do the radioactive compounds of this invention go primarily to bone tissue, they tend to concentrate in the malignant bone tissue and remain there to treat the malignant tissue. This permits the use of smaller doses of radioactive compound, thus sparing the patient from excessive radiation and keeping radiation damage to bone marrow to a minimum.

Since the radioactive compounds of this invention emit gamma rays, it is possible for the physician, after administration of the compound, to do a body scan of the patient using a gamma camera. This enables the physician to see precisely where in the patient's body the chromium-51 compound is located. The physician can thus ascertain that a therapeutic dose of the radioactive compound has gone to the site of the bone tumor. The compounds may also be used to determine the effectiveness of treatment by indicating whether or not the bone tumor has changed size or spread.

The utility of the radioactive compounds of the invention in treating bone cancer is evident from a combination of evidence. First the utility of the compounds of the invention for treating bone cancer rests upon the ability of the compounds to selectively seek out bone cancer lesions. Experiments were carried out on several dogs which had bone cancer lesions. The dogs were administered methyl diphosphate-chromium-51 compounds of the invention. As a result, the compounds of the invention did seek out the bone tumor tissues as revealed by gamma ray exposure on X-rays.

More specifically with respect to the experiments, the dogs were first injected with diagnostic material, radioactive Technetium labelled polyphosphate, to specifically locate the tumors. After the Technetium labelled polyphosphate dissipated, then the therapeutic agent of the invention containing chromium-51 was injected into the dogs, and the therapeutic agent went to precisely the same bone cancer tissues as had the diagnostic agent.

Having thus shown that the compounds of the invention seek out bone cancer tissues, it was then determined that the chromium-51 compounds are stable and remain at the bone cancer sites for at least 27 days which is the half-life for chromium-51. The continuous residence of the methyl diphosphonate-chromium-51 compounds of the invention at the bone tumor sites was shown by periodically measuring the radiation given off from the treated sites. Radiation from the chromium-51 compounds was given off continuously for 27 days thus proving that the chromium-51 compounds of the invention remain at the tumor sites for the half-life of the chromium-51.

As discussed hereinabove, an important aspect of this invention is the treatment of bone cancer lesions without harming bone marrow. The tests that were conducted on the dogs having bone cancer lesions were conducted with the understanding that bone marrow should not be adversely affected by chromium-51 compounds of the invention. This is in contrast with data from treatments with Strontium-89 and Samarium-153.

More specifically, Cr-51 is one of the largest producers of Auger low energy electrons of any radioisotope investigated. These Auger electrons travel very short distances in tissue and in fact penetrate less than alpha or beta particles. This feature leads to the calculated (and verified) value of 93 millirads of energy deposition for each disintegration of Cr-51 (27.8 day half-life). Since each curie of Cr-51 by definition is associated with $3.7 \times 10^{10}$ disintegrations per second, enormous amounts of radiation can be delivered to desired, specific tissue or sites in the human patient. The drug Cr 51-MDP is carried to the desired site, namely the tumor in man, by the attraction of MDP for bone. Since the accretion rate of tumor for MDP is substantially higher than normal bone, more of the Cr-MDP drug is deposited on tumors, whereby the efficacy of Cr-51 treatment is enhanced.

More specifically, adverse effects on bone marrow are indicated by changes in blood cell profiles. A normal blood profile for a particular individual (be it a dog or a human) contains a profile of red cells, white cells, etc. After bone marrow has been irradiated, the blood profile changes. It has been reported that blood profile changes occur after a patient is treated with Samarium-153 or Strontium-89. However, tests on dogs should provide data which show that blood profile changes do not occur during and/or after treatment with methyl diphosphonate-chromium-51 compounds of the invention. It should be clear then, by using chromium-51 compounds of the invention, bone marrow should not be adversely affected.

From the results of the above-described investigations, the compounds of the invention have been shown to be of value in treating bone cancer lesions. Furthermore, the compounds of the invention have shown no harmful or deleterious secondary or side effects.

The amount of radioactive compound to administer as a therapeutic agent is within the skill of the art to determine. The size of the dose will be determined, for example, by the type of tumor and its size and whether or not it has spread. The compound is administered intravenously as a therapeutic agent. More specific details on administration are disclosed above under the caption "Methods of Administration".

Thus, the instant invention provides novel radioactive compounds that are useful as therapeutic agents for treating tumors, particularly bone cancer, and for alleviating to some extent the pain and suffering associated therewith.

While specific embodiments of the present invention have been shown and described to illustrate the inventive principles, it is to be understood that such showing and description have been offered only by way of example and not by way of limitation. Protection by Letters Patent of this invention in all its aspects is sought to the broadest extent that the prior art allows and as set forth in the appended claims.

What is claimed is:

1. A radioactive compound comprising a bone-seeking moiety and a chromium-51 moiety.

2. The radioactive compound described in claim 1, wherein said bone-seeking moiety is selected from the group consisting of inorganic polyphosphates and organic phosphonates.

3. The radioactive compound described in claim 2, wherein said inorganic polyphosphate is a pyrophosphate.

4. The radioactive compound described in claim 1, wherein said organic phosphonates are selected from the group consisting of 1-hydroxyethane-1,1-diphosphonate, methylene diphosphonate, di-chloro methylene disphosphonate, and 1-amino-ethane-1, 1-diphosphonate.

5. A method of treating cancer which comprises administering, to a body in need of such treatment, an effective amount of a radioactive compound, comprising a bone-seeking moiety and a chromium-51 moiety.

6. A method of treating malignant bone tumors comprising administering an effective amount of the radioactive compound of claim 1 to a body.

7. A method of treating malignant bone lesions which comprises administering, to a body, an effective amount of a radioactive compound, comprising an organophosphonate selected from the group consisting of 1-hydroxyethane-1,1-diphosphonate, methylene diphosphonate, di-chloro methylene diphosphonate, and 1-amino-ethane-1,1-diphosphonate, and chromium-51.

8. A radioactive compound comprising an untagged organophosphonate precursor of the general formula

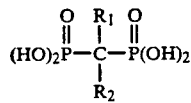

wherein $R_1$ and $R_2$ may be hydrogen, an aliphatic hydrocarbon, an aromatic hydrocarbon, an alicyclic hydrocarbon and wherein either $R_1$ or $R_2$ may be an hydroxyl group; and wherein said organophosphonate is tagged with chromium-51.

9. The radioactive compound of claim 8, wherein $R_1$ is a hydroxyl group and $R_2$ is a methyl group.

10. The radioactive compound of claim 8, wherein $R_1$ and $R_2$ are the same.

11. The radioactive compound of claim 9, wherein $R_1$ and $R_2$ are both hydrogen.

12. The radioactive compound of claim 9, wherein $R_1$ and $R_2$ are different.

13. The radioactive compound of claim 8, wherein $R_1$ is hydrogen and $R_2$ is a methyl group.

14. A method of treating metastatic bone cancer by administering, to a patient, an effective amount of a radioactive compound comprising an untagged organophosphonate precursor of the general formula

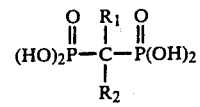

wherein $R_1$ and $R_2$ may be hydrogen, an aliphatic hydrocarbon, an aromatic hydrocarbon, an alicyclic hydrocarbon and wherein either $R_1$ or $R_2$ may be a hydroxyl group; and wherein said organophosphonate is tagged with chromium-51.

15. A method of treating cancer comprising administering an effective amount of the radioactive compound of claim 8 to a body in need of such treatment.

16. A method of treating bone cancer described in claim 14 wherein, in the radioactive compound used for treatment, $R_1$ is a hydroxyl group and $R_2$ is a methyl group.

17. A method of treating malignant bone tumors comprising administering an effective amount of the radioactive compound of claim 8 to a body.

18. A method of treating malignant bone lesions comprising administering an effective amount of the radioactive compound of claim 9 to a body.

19. A method of treating bone cancer, comprising the steps of selecting an organophosphonate precursor compound of the general formula

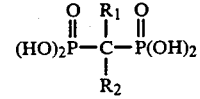

wherein $R_1$ and $R_2$ may be hydrogen, an aliphatic hydrocarbon, an aromatic hydrocarbon, an alicyclic hydrocarbon; and wherein either $R_1$ or $R_2$ may be an hydroxyl group having an affinity for bone, tagging the precursor compound with a chromium-51 radioisotope which emits low energy Auger electrons and does not emit high energy beta particles which would be potentially harmful to surrounding healthy tissue, said radioisotope having a half-life that facilitates preparation of the tagged compound at a central location and delivery of the same through available transportation channels, and administering the tagged compound to a patient in need thereof.

20. The method of claim 19, wherein said precursor compound is 1-hydroxyethlidene, bis (EHDP), and wherein said radioisotope is chromium-51.

21. The method of claim 19, wherein said organophosphonate is a methylene diphosphonate (MDP).

22. The method of claim 19, wherein said compound is an analog of methylene diphosphonate.

23. A radioactive compound comprising a chromium-51 labelled organophosphonate of the general formula

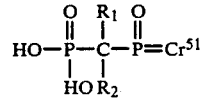

, wherein $R_1$ and $R_2$ may be hydrogen, an aliphatic hydrocarbon, an aromatic hydrocarbon, an alicyclic hydrocarbon, and wherein either $R_1$ or $R_2$ may be an hydroxyl group.

24. A radioactive compound comprising a chromium-51 labelled organophosphonate of the formula

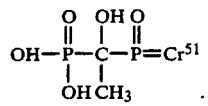

25. A radioactive compound comprising a chromium-51 labelled organophosphonate of the general formula

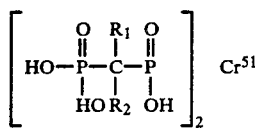

, wherein $R_1$ and $R_2$ may be hydrogen, an aliphatic hydrocarbon, an aromatic hydrocarbon, an alicyclic hydrocarbon, and wherein either $R_1$ or $R_2$ may be an hydroxyl group.

26. A radioactive compound comprising a chromium-51 labelled organophosphonate of the formula

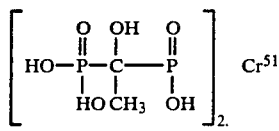

27. A radioactive compound described in claim 23, wherein $R_1$ and $R_2$ are hydrogens.

28. A radioactive compound described in claim 25 wherein $R_1$ and $R_2$ are hydrogens.

29. A method of treating bone cancer by administering to a patient, an effective amount of a radioactive compound comprising a chromium-51 labelled organophosphonate of the general formula

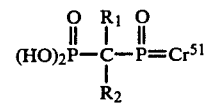

wherein $R_1$ and $R_2$ may be hydrogen, an aliphatic hydrocarbon, an aromatic hydrocarbon, an alicyclic hydrocarbon and wherein either $R_1$ or $R_2$ may be a hydroxyl group.

30. A method of treating bone cancer by administering to a patient, an effective amount of a radioactive compound comprising a chromium-51 labelled organophosphonate of the general formula

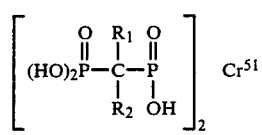

wherein $R_1$ and $R_2$ may be hydrogen, an aliphatic hydrocarbon, an aromatic hydrocarbon, an alicyclic hydrocarbon and wherein either $R_1$ or $R_2$ may be a hdroxyl group.

* * * * *